April 28, 1959 LEE ROY TEAGUE Plant Pat. 1,827
STRAWBERRY PLANT
Filed Aug. 26, 1958
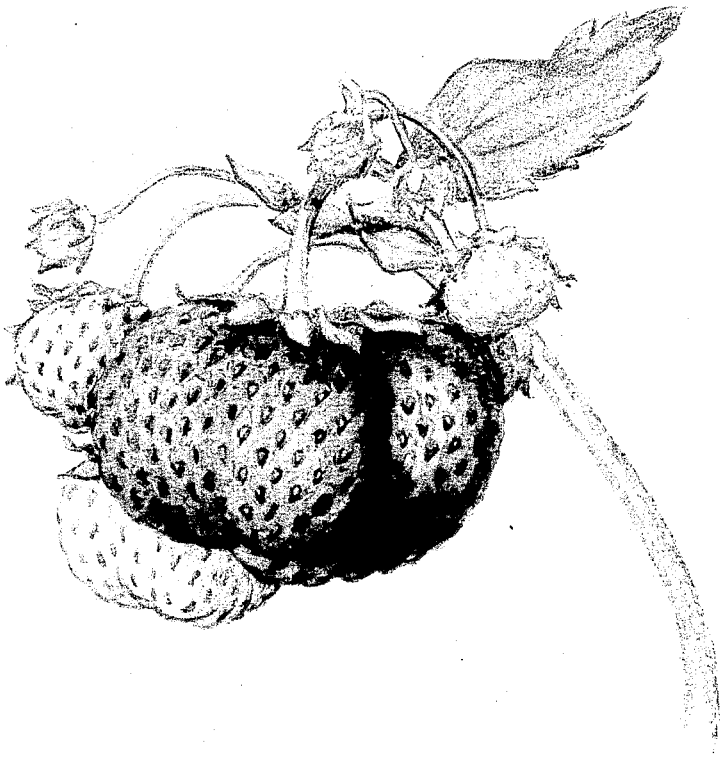
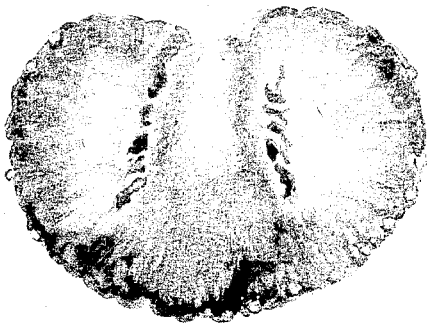
INVENTOR
Lee Roy Teague
By Orville M. Kile
PLANT PATENT AGENT United States Patent Office Plant Pat. 1,827
Patented Apr. 28, 1959

1,827

STRAWBERRY PLANT

Lee Roy Teague, Logan, Iowa

Application August 26, 1958, Serial No. 757,435

1 Claim. (Cl. 47—62)

My present discovery relates to an improved variety of everbearing strawberry plant producing large quantities of large, marketable berries of good flavor and substance.

This variety is a chance seedling found by me a few years ago just outside a patch of the varieties Red Rich (Plant Patent No. 993), Superfection (unpatented), and Streamliner (unpatented) as grown in my garden in Logan, Iowa. It bears some of the characteristics of each of the three varieties named, but its parentage is not definitely known.

I have asexually reproduced this new variety in my gardens in Logan, by means of runners, and its characteristics appear to be permanent.

Accompanying illustrations show a cluster of the berries of my new variety in varying stages of maturity, and a cross-section of a fully-ripened berry—all in approximately true colors.

In the following detailed description, color plate numbers indicate Ridgway's Color Standards and Nomenclature. Where no plate number is mentioned, the ordinary dictionary meaning of the term is intended.

*The plant*

Type: Everbearing. Self-pollinizing.

Growth: Large and vigorous. Plants measure 6 to 8 inches high above the crowns and consist of many leaf branches and when in heaviest bearing season have 2 to 5 heavy fruit stems, the latter more than half the height of the leaves.

Fruit stems: Strong and upright, tending to hold the berries well up from the ground and free from dirt. Each of these stems bears a large cluster of berries in various stages of growth.

Roots: Long and profuse; strong and vigorous.

Runners: Numerous; heavy; easily controlled.

Production: Heavy producer, with long-bearing season extending from early June until freezing time.

Flower: Perfect. Large, measuring approximately 1 inch in diameter. White. Sepals numerous. Stamens yellow-tinted, changing to brown as the white petals fall.

Marketability: Fruit is firm and keeps well both on plant and after picking, thus making it very marketable.

Foliage:

*Type.*—Trifoliate.

*Size and quality.*—Large and of heavy texture. Each of the three leaflets measures about 2½ to 3 inches in length as well as in width.

*Color.*—Medium green, approximately Light Elm Green to Forest Green (Pl. XVII).

*Appearance.*—Venation is prominent and serrations deep.

*Leaf stems.*—Red-tinged; hairy; 6 to 8 inches tall.

*Fruit*

Form: Flattened. Rounded (not pointed) on blossom end; flat on stem end, permitting cleaning without waste.

Size: Medium; uniform.

Color: Deep dark red, being approximately Nopal Red, shaded with Carmine (both Pl. I). Ripens evenly.

Calyx: Large; many sepals; flat; adheres well.

Surface: Seeds medium; not too prominent.

Flesh:

*Color.*—Dark red color goes all the way through berry, with center of Carmine surrounded by Nopal Red. No white core.

*Flavor.*—Sub-acid and pleasing.

*Firmness.*—Flesh is very firm; no hard core.

*Juiciness.*—Medium.

Having thus disclosed my discovery, I claim:

The new and distinct variety of everbearing strawberry plant, characterized particularly by its vigor of growth; its numerous but easily controlled runners; its long season of fruit production; its even ripening; and its heavy production of fruit of pleasing flavor, uniform size, broadly rounded shape with flat stem end, and firm flesh which is dark red all the way through.

No references cited.